United States Patent [19]
Szentmiklosi et al.

[11] Patent Number: 4,814,336
[45] Date of Patent: Mar. 21, 1989

[54] METHOD OF TREATING A VASCULAR OBSTRUCTIVE LESION RESULTING FROM RESTRICTED BLOOD CIRCULATION

[75] Inventors: Peter Szentmiklosi; Istvan Hermecz; Zoltan Meszaros; Laszlo Tardos; Jeno Marton; Lelle Vasvari (nee Debreczy); Agnes Horvath, all of Budapest; Katalin Marmarosi (nee Kellner), Biatorbagy, all of Hungary

[73] Assignee: CHINOIN Gyogyszer es Vegyeszeti Termekek Gyara Rt, Budapest, Hungary

[21] Appl. No.: 937,536

[22] Filed: Dec. 3, 1986

[30] Foreign Application Priority Data

Dec. 4, 1985 [HU] Hungary .................................. 4639

[51] Int. Cl.[4] ...................... A61K 31/52; A61K 31/47

[52] U.S. Cl. .................................. 514/263; 514/264; 514/265; 514/307

[58] Field of Search ................ 514/263, 264, 265, 307

[56] References Cited

U.S. PATENT DOCUMENTS 4,035,366 7/1977 Szentmiklosi et al. ............ 514/878

OTHER PUBLICATIONS

Aviado et al, *Pharmacology of Pentoxifylline: A Hemorheologic Agent for the Treatment of Intermittent Claudication,* Angiology–Journal of Vascular Diseases, pp. 407–417 (Jul. 1984).

*Primary Examiner*—Frederick E. Waddell
*Attorney, Agent, or Firm*—Herbert Dubno; Jonathan Myers

[57] ABSTRACT

A new method of treatment is disclosed for a vascular obstructive lesion resulting from restricted blood circulation, characterized by an erythrocyte pathology, in an effected animal subject. The new method involves the administration of 1-(3′,4′-diethoxybenzyl)-6,7-diethoxy-3,4-dihydroisoquinolinium-theophylline-7-acetat e, in a dosage and at a rate sufficient to maintain a blood concentration of at least 0.5 to at most 3 $\gamma$/ml, calculated on the basis of 1-(3′,4′-diethoxybenzyl)-6,7-diethoxy-3,4-dihydroisoquinoline.

1 Claim, 2 Drawing Sheets

METHOD OF TREATING A VASCULAR OBSTRUCTIVE LESION RESULTING FROM RESTRICTED BLOOD CIRCULATION

The invention relates to a process for treating pathological conditions caused by vascular obstructive lesions resulting from restricted microcirculation of the blood by using an appropriate dose of a pharmaceutical composition containing 1-(3',4'-diethoxybenzyl)-6, 7-diethoxy-3, 4-dihydroisoquinolinium-theophyllin-7-acetate (further on: Depogen) as active ingredient.

It is known that Depogen U.S. Pat. No. 4,035,366 has a peripheral vasodilating effect and decreases the extremital vascular resistence (Acta Pharmaceutica Hung. 49, 50-53 (1979)), when administered to patients in doses up to 300 mg/day.

It is also known that the arterisclerotic diseases—mainly in the well developed industrial countries—are widespread diseases and are first among mortality causes. In the case of people suffering from the above clinical picture—patients suffering from obliterating vascular process of the lower leg (claudication) or from vascular encephalopathy—the wall of the resistance arteries will be thicker, the number of the vegetative receptors decreases, the elasticity and flow through the arteries deteriorate.

For drug treatment of such patients peripheral vasodilating agents have been used. When the sclerotic arteries are, however, in very bad condition, they are less dilatable; thus the possibility of using such agents is limited (Martindale: The extra Pharmacopeia XXVIIIth Ed. (1982) London, P. 1614).

Furthermore genetic, hereditary diseases are known where the transformation of the erythorcytes into sickle cells or the loss of their flexibility are manifested in significant clinical symptoms (Sickle cell anemia). (Dorlando illustrated Medical Dictionary 25, 860 Ed. Sanders (1974)). The therapy of this illness has not succeeded with the usual drugs either (Klinische Pharmakologie und Pharmakotherapie Kunmerle, Garett, Tzyzi Urban, Schwarzenberg Munchen, 1976, p. 911).

It is also known that the 3,7-dihydro-3,7-dimethyl-1--(5-oxohexyl)-1H-purine-2,6-dione(penthoxiphylline; (Trental ®)) improves some rheological parameters of the blood, first of all the plasticity of the erythrocytes and thus it can be used for treating clinical pictures, where the deterioration of the plasticity of the erythrocytes causes bad microcirculation and secondary tissue hypoxia, with good results (Angiology 36, 4, 226–234 (1985)).

By improving the filtrability the erythrocytes may pass through the capillaries more easily and thus the oxygen supply of the tissues improves significantly. While influencing the haemorheological properties of the blood, namely increasing its fluidity, many pathological conditions may be influenced favorably (e.g. decreasing the danger of thrombosis after operations, prophylaxis of myocardial infarct, hard to heal wounds caused by bad blood supply, ulcus, embolism, cerebral infarct, shock chronic vascular diseases, claudication, senile cerebral circulatory disturbances, diabetes) thus this has a great therapeutical importance both systematically and locally.

It has been found that Depogen when administered in suitable doses possess very favorable haemorheological properties. It increases the filtrability of the pathological human erythrocytes significantly as proved by both ex vitro and in vivo tests.

The preferred dose is 400 to 800 mg/day in a sustained-release tablet or capsule and the medicine is generally administered to the patient for a period of at least 10 days. Preferably the dosage is 5.5 to 14 mg/kg of body weight per day.

For the examination of the in vitro filtrability of the erythrocytes the method of Teitel (Nouv. Rev. Franc. Haematol. 7. 195 (1967)) was used where the filtration rate of concentrated erythrocyte suspension was measured. In the test fresh, normal erythrocytes, fresh in hyperosmotic solution shrunken erythrocytes and erythrocytes stored in CPD blood-conserving solution contracted for 30 days at +4° C. were used. The results are given in FIGS. 1 and 2 (the filtrability of the contracted erythrocytes and that of the erythrocytes stored for 30 days were given as the % of the filtrability of the control fresh, normal erythrocytes.)

Figure 1:
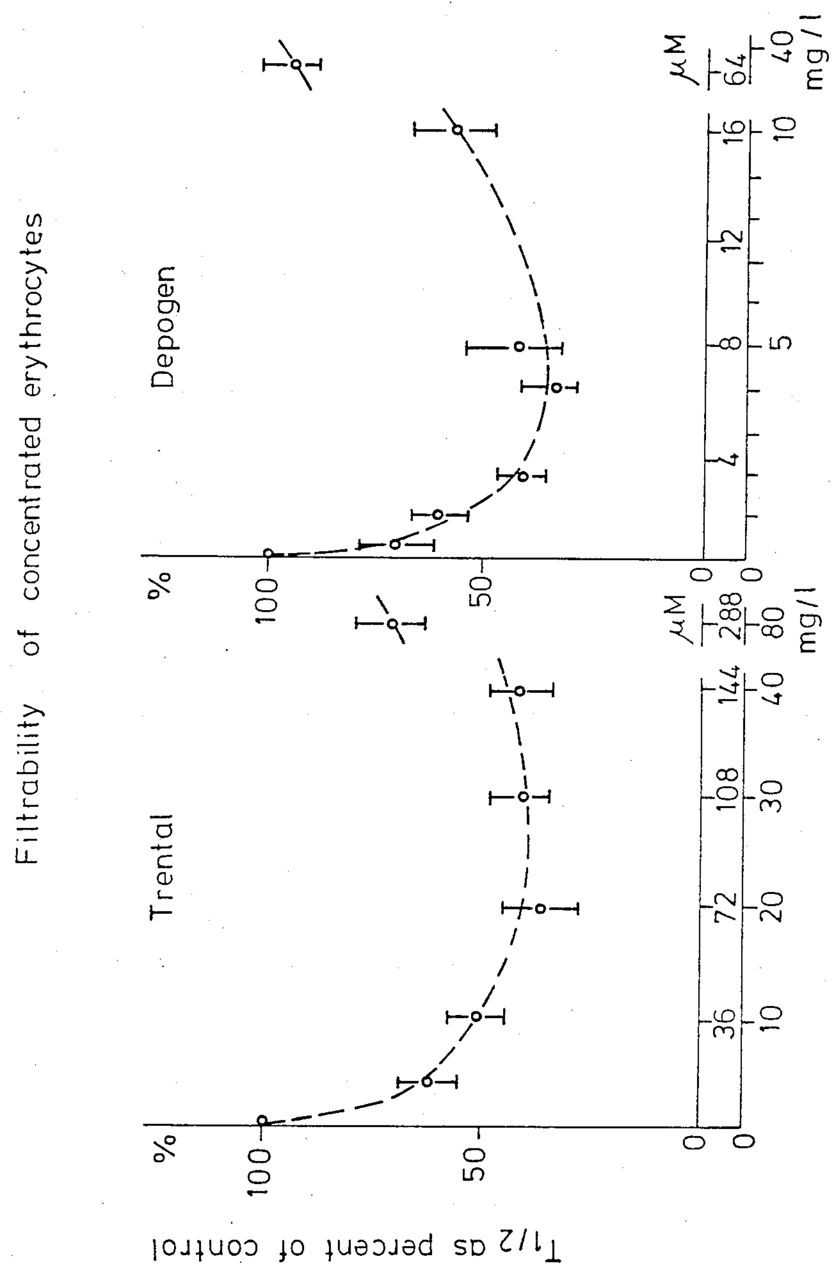
FIG. 1 is a set of two graphs in which the filtration half-times ($T_{\frac{1}{2}}$) for contracted (shrunken) erythrocytes are plotted along the Y-axis as a percentage of the filtration half-time for normal erythrocytes (control) against doses of respectively Trental and Depogen.
Figure 2:
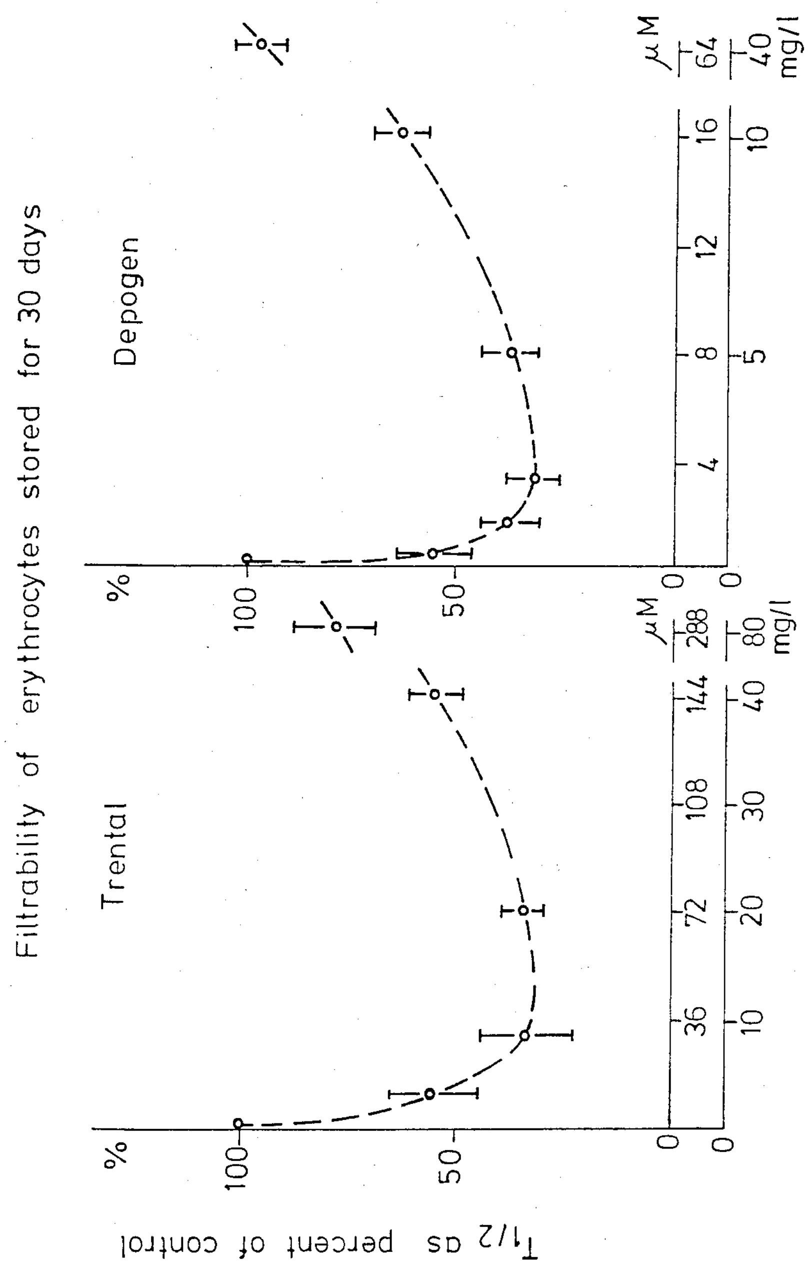
FIG. 2 is a set of two graphs in which the filtration half-time ($T_{\frac{1}{2}}$) for erythrocytes stored for 30 days are plotted along the Y-axis as a percentage of the filtration half-time for normal erythrocytes (control) against doses of respectively Trental and Depogen.

From FIGS. 1 and 2 it may be seen that both Trental$^R$ and Depogen increase the filtrability of the erythrocytes significantly, i.e. decrease $T_{\frac{1}{2}}$-value characteristic for the filtration (the time which is needed for the filtration of the half amount of the erythrocytes). The effect depends in the case of both drugs on the doses. The optimal effect may be achieved with Depogen in lower concentration interval (0.5 to 1.5 μumol) than in case of Trental (5 to 10 μumoles). Besides Depogen exerts the same effect as Trental in a 10 to 25-times lower concentration as shown by the concentration necessary for the half-maximal effect ($ID_{50}'$, Table I).

TABLE I

| | Trental $ID_{50}$ μmol | Depogen $ID_{50}$ μmol | Rel. activity Depogen/Trental |
|---|---|---|---|
| contracted erythrocytes | 36 | 2.2 | 16.3 |
| erythrocytes stored for 30 days | 15.8 | 0.5 | 31.6 |

The clinical examinations carried out on patients suffering from lower leg and cerebral obliterating vascular diseases gave the following results: 41 patients were treated for 10 days in a dose of 450 mg/day Depogen or Trental orally (beside 5 healthy controls). The favorable effect of Depogen in cerebral vascular disease has been found, the symptoms have decreased. The results of the examinations carried out with EEG and ECHO are given in Tables 2 and 3. In the case of lower leg obliteration the two drugs have the same effect.

The filtrability of the erythrocytes is much lower ($T_{\frac{1}{2}}$average =18.15 min) compared to the healthy control ($T_{\frac{1}{2}}$average =8.7 min; ($T_{\frac{1}{2}}$normal =6.5 to 10.5 min) before treatment. During a 10 day Depogen-treatment the filtrability of the erythrocytes has been normalized ($T_{TM}$average =9.53 min) in most cases for the patients independently of whether the patient had cerebral or lower leg disease. This effect was much more stronger than in the case of patients treated with Trental although the treatment was also in this case successful ($T_{TM}$average =12.1 min). The improvement in the filtrability of the erythrocytes correlated to the decrease of the clinical symptoms.

The filtrability of the erythrocytes was at the healthy controls unchanged ($T_{TM}$average =8.7 min).

It has been surprisingly found that when the decrease of the filtrability half-time ($T_{TM}$average) of the erythrocytes was higher, the therapeutic effect was also higher.

In view of the above described, the treating process according to the invention is also suitable for determining the dose used in the treatment, for preindication of the necessity of the therapy or for that of the efficiency of the treatment in view of the filtrability of the erythrocytes determined from the blood of the patient. Preferably a daily dose of 400 to 800 mg. is used which is necessary for achieving a drug blood concentration of at least 0.5 to at most 3 $\gamma$/ml calculated on the basis of the 1-(3',4-diethoxybenzyl)-6,7-diethoxy-3,4-dihydroisoquinoline.

In the treating process the drug may be used in the form of capsules, tablets, sustained-release tablets, injections, solutions or syrups in colus or infusion, preferably sustained-release.

EXAMPLE 1

DEPOGEN SUSTAINED-RELEASE TABLET

Depogen 40.00 Units
CMC-Na 5.50
Gypsum 52.90
Stearic acid 4.80
Tween 85 0.15
Tween 20 0.10
CMC-Na 3.00
Mg-stearate 1.00
Talcum 2.00

EXAMPLE 2

DEPOGEN CAPSULE

Depogen 150 mg
Aerosil 300 3 mg
Kollidon V.A. 64 12 mg
Amylum mais 54 mg
Avicel 66 mg
Cutine H.R. 3 mg
Mg-stearate 3 mg
Talcum 9 mg

EXAMPLE 3

Depogen 1.00 g
Cacao powder 10.00 g
Saccharosum 45.00 g
Glycerinum 5.00 g
Natrium chloratum 0.05 g
Solutio conservans 0.50 g
Spiritus dilutus 2.00 g
Aqua destillata ad 100.00 g

EXAMPLE 4

Depogen 40.00 mg
Spir. conc. 0.04 ml
Aqua bidestillata ad 1.00 ml

EXAMPLE 5

Depogen 0.15 g
Witepsol H 32 2.57 g
Tagat R-1 0.14 g
Softisan 378 0.14 g

EXAMPLE 6

Depogen 40 g (or stoichiometric equivalent quantity of monohydrate
Endragit 1 100-55 8 g
Sodium Hydroxide 0.08 g
Aerosil R 972 0.3 g
Magnesium Stearage AD 50 g

TABLE 2

| | The effect of Trental and Depogen on the result of the EEG examination | | | |
|---|---|---|---|---|
| | unchanged | deteriorated | improved | total |
| TRENTAL | 5 (55.5%) | 0 | 4 (44.5%) | 9 |
| DEPOGEN | 1 (12.5%) | 0 | 7 (87.5%) | 8 |

TABLE 3

| | The effect of Trental and Depogen on the result of the ECHO examination | | | |
|---|---|---|---|---|
| | unchanged | deteriorated | improved | total |
| TRENTAL | 9 (100%) | 0 | 0 | 9 |
| DEPOGEN | 7 (87.5%) | 0 | 1 (12.5%) | 8 |

We claim:

1. A method of improving the filterability and plasticity of erythrocytes through the vasculature of a patient in need of said treatment, which comprises the step of orally administering to the patient in the presence of a clinical picture of deteriorated erythrocyte plasticity and secondary tissue hypoxia, 1-(3',4'-diethoxybenzyl)-6,7-diethoxy-3,4-dihydroiso quinoline-theophyllin-7-acetate, in a dosage of 400 to 800 mg per day, and sufficient to maintain a blood concentration of at least 0.5 to at most 3.0 micrograms/ml, calculated on the basis of 1-(3',4'-diethoxybenzyl)-6,7-diethoxy-3,4-dihydroisoquinoline, thereby enhancing plasticity of the erythrocytes in said vasculature and the filterability of circulating erythrocytes therethrough.

* * * * *